(12) United States Patent
Tsuyuki

(10) Patent No.: US 10,010,305 B2
(45) Date of Patent: Jul. 3, 2018

(54) MEDICAL SYSTEM, SERVER APPARATUS, AND POWER MANAGEMENT METHOD

(71) Applicant: TOSHIBA MEDICAL SYSTEMS CORPORATION, Otawara-shi, Tochigi-ken (JP)

(72) Inventor: Masaharu Tsuyuki, Nasushiobara (JP)

(73) Assignee: TOSHIBA MEDICAL SYSTEMS CORPORATION, Otawara-Shi (JP)

( * ) Notice: Subject to any disclaimer, the term of this patent is extended or adjusted under 35 U.S.C. 154(b) by 545 days.

(21) Appl. No.: 14/338,843

(22) Filed: Jul. 23, 2014

(65) Prior Publication Data

US 2014/0334597 A1 Nov. 13, 2014

Related U.S. Application Data

(63) Continuation of application No. PCT/JP2013/051646, filed on Jan. 25, 2013.

(30) Foreign Application Priority Data

Jan. 25, 2012 (JP) .................................. 2012-013381

(51) Int. Cl.
*A61B 6/00* (2006.01)
*H05G 1/08* (2006.01)
(Continued)

(52) U.S. Cl.
CPC ............ *A61B 6/56* (2013.01); *A61B 5/055* (2013.01); *A61B 6/032* (2013.01); *A61B 6/54* (2013.01);
(Continued)

(58) Field of Classification Search
CPC ........... A61B 5/055; A61B 6/03; A61B 6/032; A61B 6/461; A61B 6/481; A61B 6/488;
(Continued)

(56) References Cited

U.S. PATENT DOCUMENTS

| 8,532,260 B2 * | 9/2013 | Takae | A61B 6/4405 378/102 |
| 2005/0259782 A1 * | 11/2005 | Kasuya | A61B 6/032 378/15 |

(Continued)

FOREIGN PATENT DOCUMENTS

| JP | 2005-245548 A | 9/2005 |
| JP | 2007-298229 A | 11/2007 |

(Continued)

OTHER PUBLICATIONS

Chinese Office Action with its English Summary for Chinese Patent Application No. 201380000124.3 dated Dec. 2, 2014.

(Continued)

*Primary Examiner* — Irakli Kiknadze
(74) *Attorney, Agent, or Firm* — Kenichiro Yoshida

(57) ABSTRACT

A medical apparatus includes an apparatus main body (11) configured to execute imaging or treatment of an object in accordance with an imaging plan or a treatment plan, an electric power calculation unit (29) configured to calculate an electric power required for the imaging or the treatment based on the imaging plan or the treatment plan, a communication unit (23) configured to receive power information from a plurality of other medical apparatuses, a total electric power calculation unit (30) configured to calculate a total electric power from the calculated electric power and the received electric power, a comparing unit (31) configured to compare the calculated total electric power with a threshold, and a display (25) configured to display a comparison result obtained by the comparing unit.

19 Claims, 10 Drawing Sheets

(51) Int. Cl.
*A61B 5/055* (2006.01)
*A61N 5/10* (2006.01)
*A61B 90/00* (2016.01)
*A61B 6/03* (2006.01)

(52) U.S. Cl.
CPC .............. *A61B 90/37* (2016.02); *A61N 5/103* (2013.01); *A61N 5/1064* (2013.01); *A61B 6/03* (2013.01); *A61B 6/461* (2013.01); *A61B 6/481* (2013.01); *A61B 6/488* (2013.01); *A61B 6/58* (2013.01)

(58) Field of Classification Search
CPC .... A61B 6/54; A61B 6/56; A61B 6/58; A61B 90/37; A61B 6/145; A61B 8/06; A61B 90/06; A61B 2017/22088; A61B 6/4291; A61B 2017/00; A61B 6/4233; A61B 6/04; A61B 6/4266; A61B 6/467; A61B 6/548; A61B 5/4836; A61B 6/4021; A61B 6/4028; A61B 6/4085; A61B 6/4488; A61B 17/2202; A61B 17/12045; A61B 2017/00969; A61B 2017/12127; A61B 2017/22038; A61B 2017/22069; A61B 2017/22021; A61B 2017/22082; A61B 2017/00084; A61B 2017/22002; A61B 2017/22028; A61B 2017/00057; A61B 2018/00023; A61B 2018/00648; A61B 2018/00797; A61N 5/103; A61N 5/1064

USPC ........................................... 378/4, 91, 92, 98
See application file for complete search history.

(56) References Cited

U.S. PATENT DOCUMENTS

| | | | |
|---|---|---|---|
| 2008/0152073 A1* | 6/2008 | Fujimoto | A61B 6/032 378/8 |
| 2009/0040061 A1* | 2/2009 | Golunski | G07C 3/08 340/683 |
| 2010/0220838 A1* | 9/2010 | Kobayashi | A61B 6/4233 378/189 |

FOREIGN PATENT DOCUMENTS

| JP | 2008000499 A | * | 1/2008 |
|---|---|---|---|
| JP | 2009-142301 A | | 7/2009 |
| JP | 2010-273782 A | | 12/2010 |
| JP | 2011-253727 A | | 12/2011 |

OTHER PUBLICATIONS

International Search Report (in English) and International Preliminary Report on Patentability corresponding to International Application No. PCT/JP2013/051646 dated May 7, 2013.

* cited by examiner

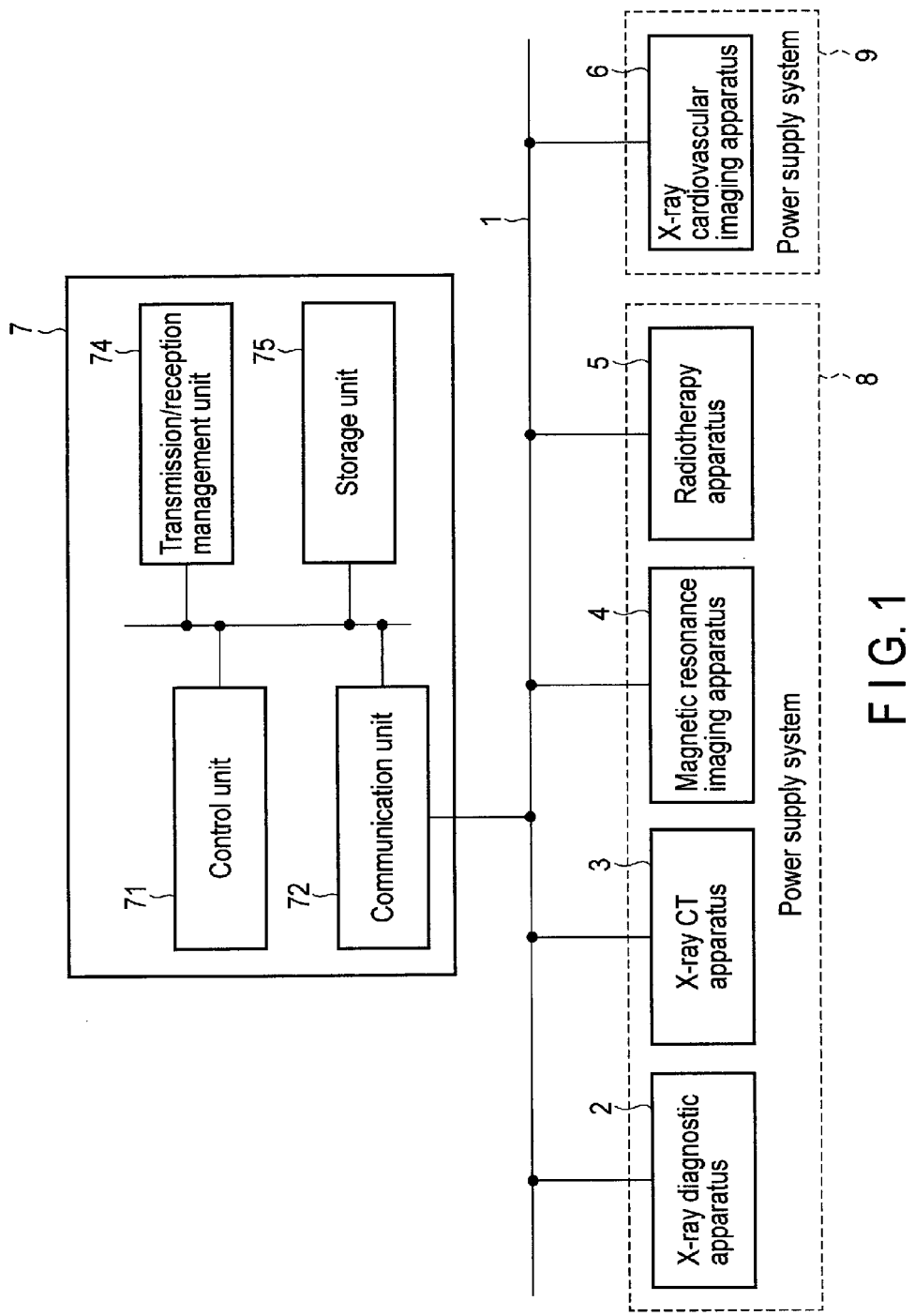
F I G. 1

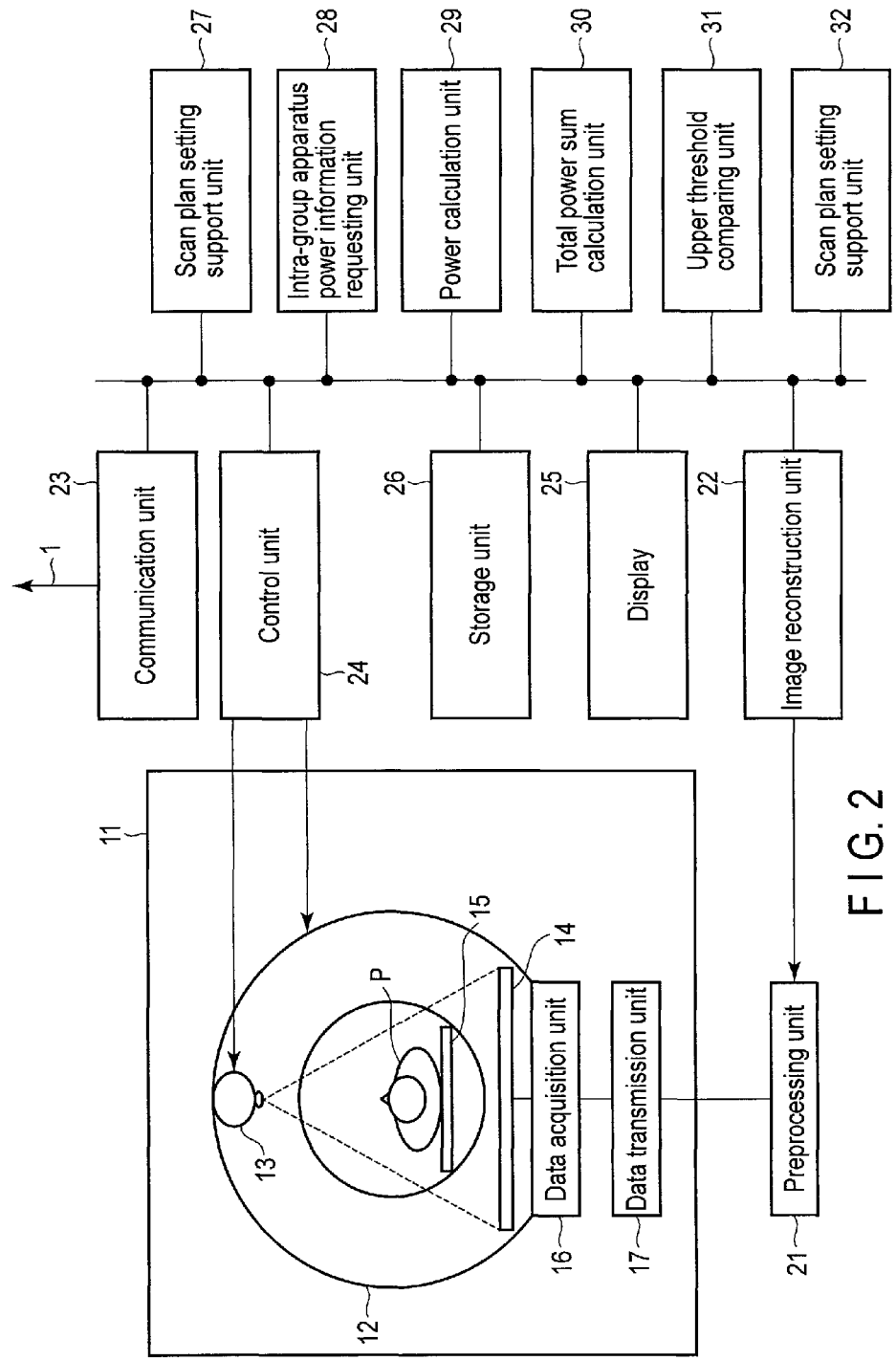
F I G. 2

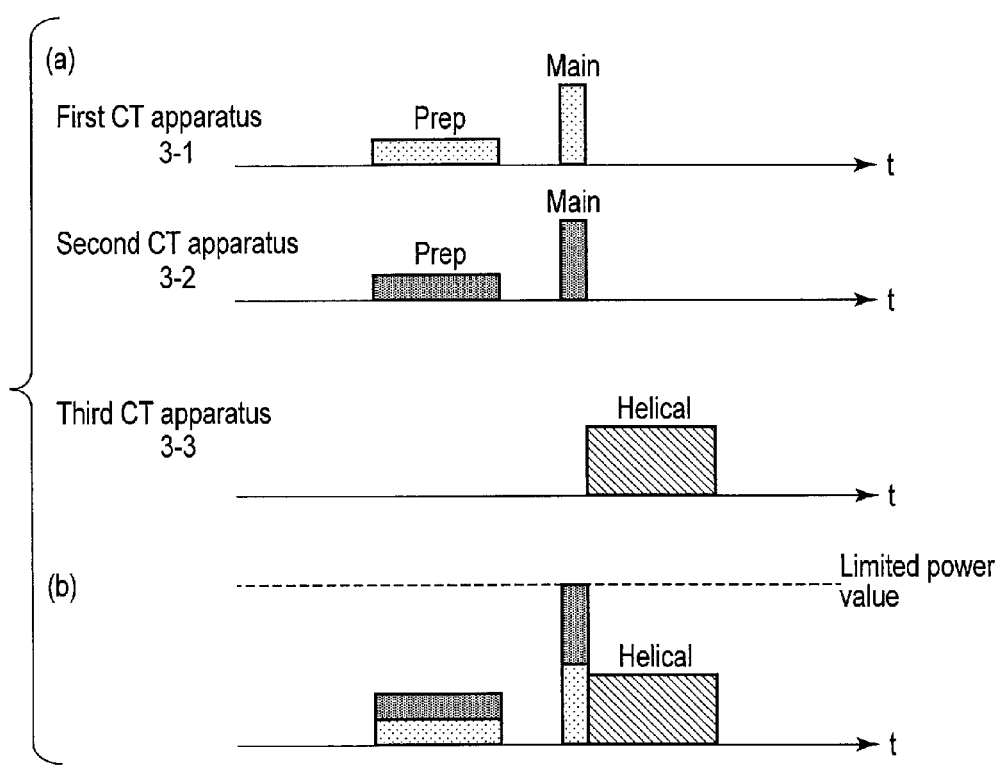
F I G. 3

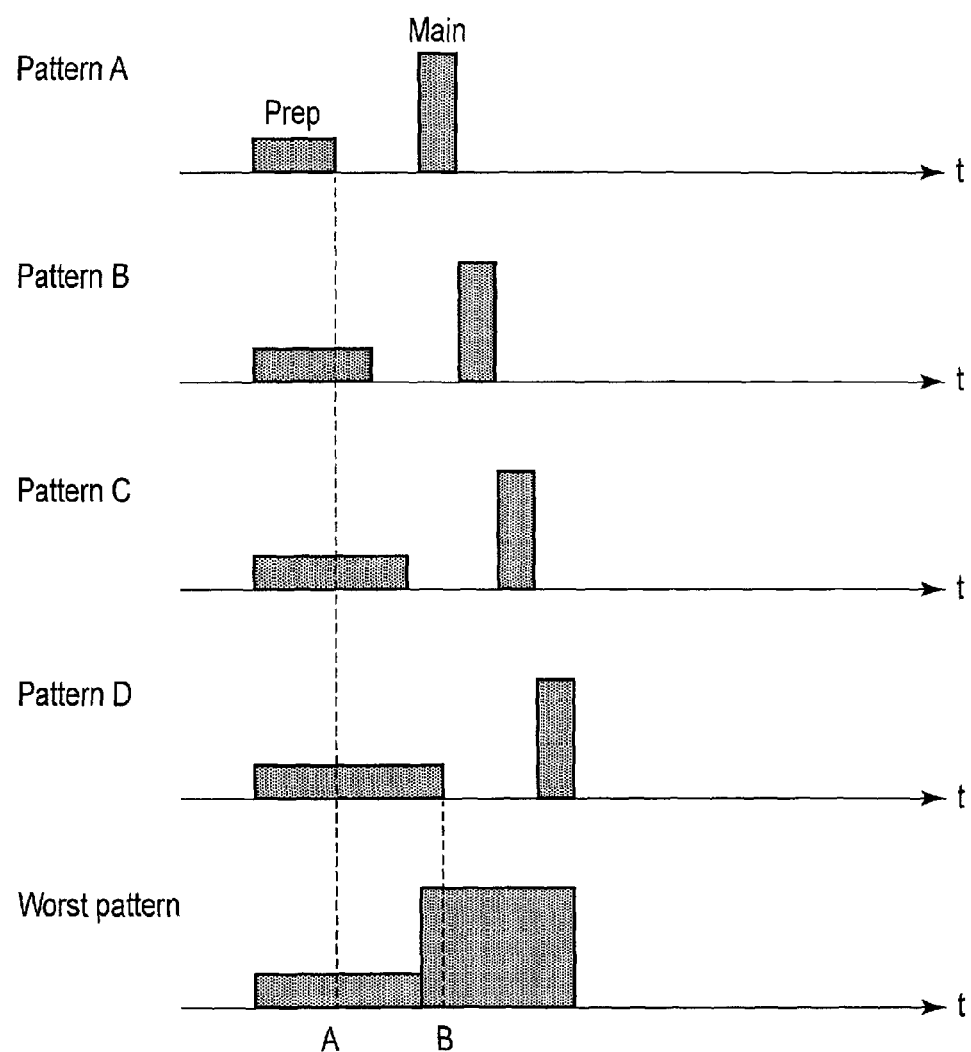
F I G. 4

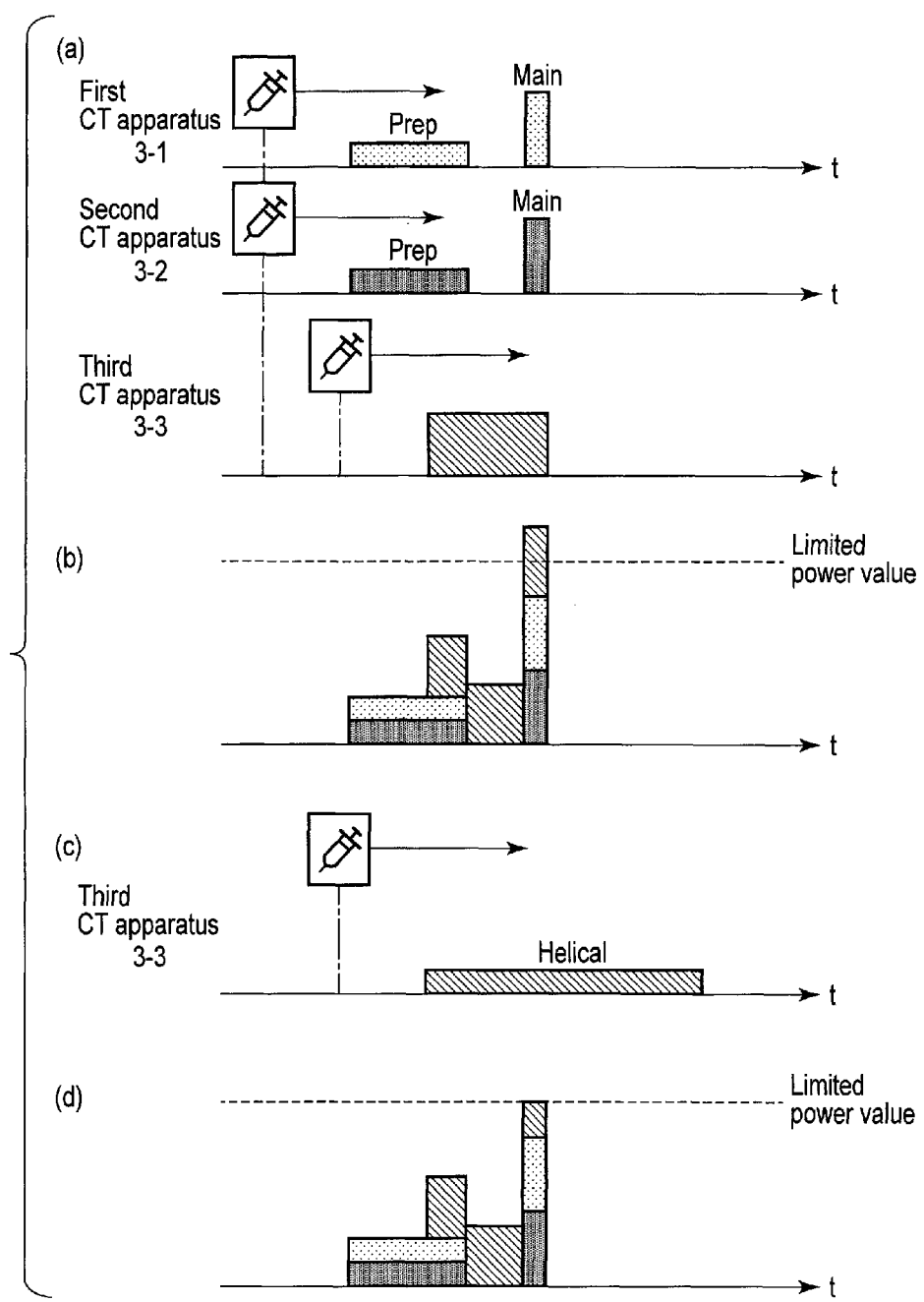
F I G. 6

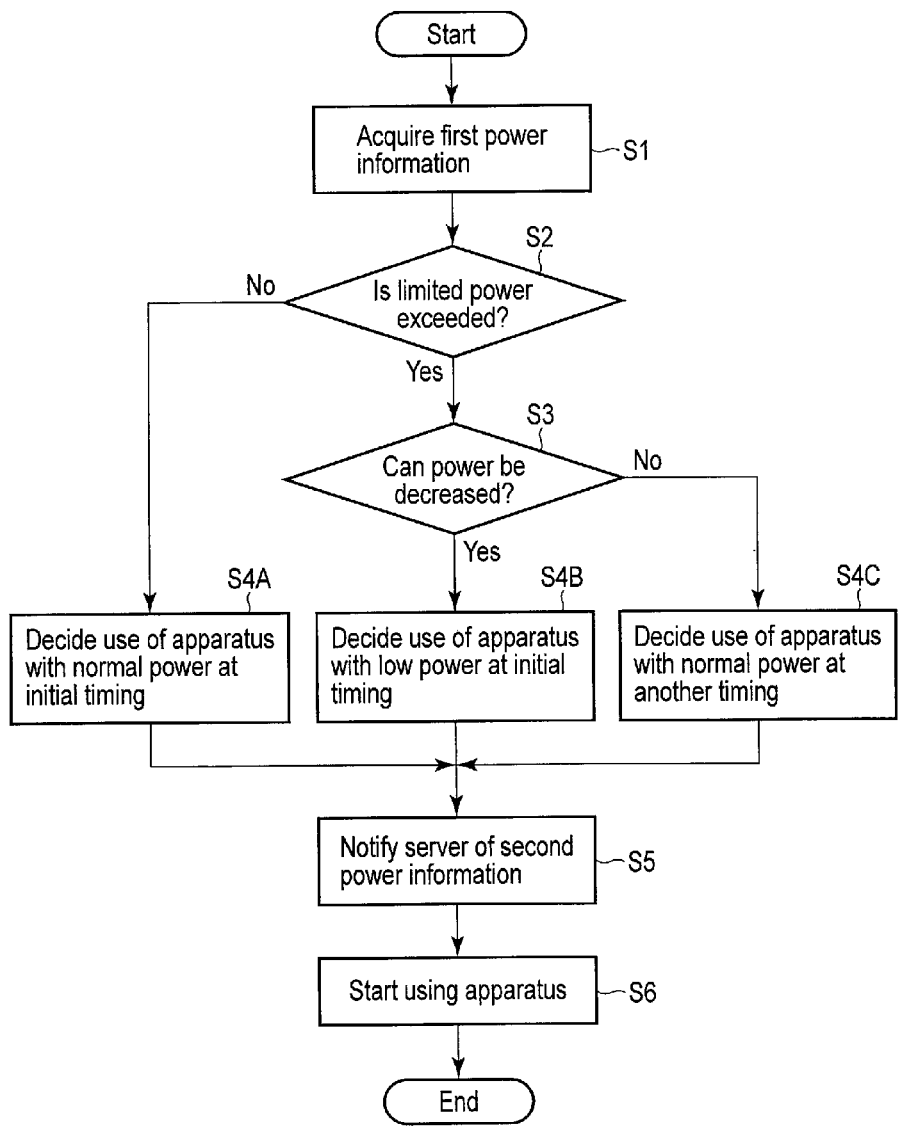
F I G. 7

MEDICAL SYSTEM, SERVER APPARATUS, AND POWER MANAGEMENT METHOD

CROSS-REFERENCE TO RELATED APPLICATIONS

This application is a Continuation application of PCT Application No. PCT/JP2013/051646, filed Jan. 25, 2013 and based upon and claiming the benefit of priority from Japanese Patent Application No. 2012-013381, filed Jan. 25, 2012, the entire contents of all of which are incorporated herein by reference.

FIELD

Embodiments described herein relate generally to power management on a medical apparatus such as an X-ray CT apparatus.

BACKGROUND

When concurrently using various types of apparatuses in a range in which they are connected to each other in a network, it is necessary to consider the total electric power to be used. The same applies to a hospital or health clinic using medical apparatuses. Even if, however, the power used approaches the limit, the operator cannot sometimes stop the use of a medical apparatus.

Conventionally, in the use of an X-ray CT apparatus, at least one of the X-ray tube voltage and the X-ray tube current is suppressed so as not to exceed the maximum operating power limit of the X-ray CT apparatus. However, this power limit degrades image quality. In addition, since a power consumption is allocated to each apparatus, it is sometimes impossible to perform an examination using high power. Furthermore, since power is limited by only limiting the number of apparatuses which can be operated at the same time, it sometimes takes a long time to start an examination even if the power is sufficient.

It is an object to avoid influences due to the operating power limit of a power supply system.

BRIEF DESCRIPTION OF THE DRAWINGS

FIG. 1 is block diagram showing the overall arrangement of a medical system according to an embodiment.

FIG. 2 is a block diagram showing the arrangement of an X-ray CT apparatus in FIG. 1.

FIG. 3 shows pieces of power information scheduled to be used by a plurality of X-ray CT apparatuses connected to a network and a basic concept based on the addition of these pieces of power information in this embodiment.

FIG. 4 is a schematic view showing the second power information in consideration of the end timing of a prep scan by an X-ray CT apparatus in this embodiment.

FIG. 6 shows an example of the use of an X-ray CT apparatus with low power in this embodiment.

FIG. 7 is flowchart in this embodiment.

DETAILED DESCRIPTION

Figure 5:
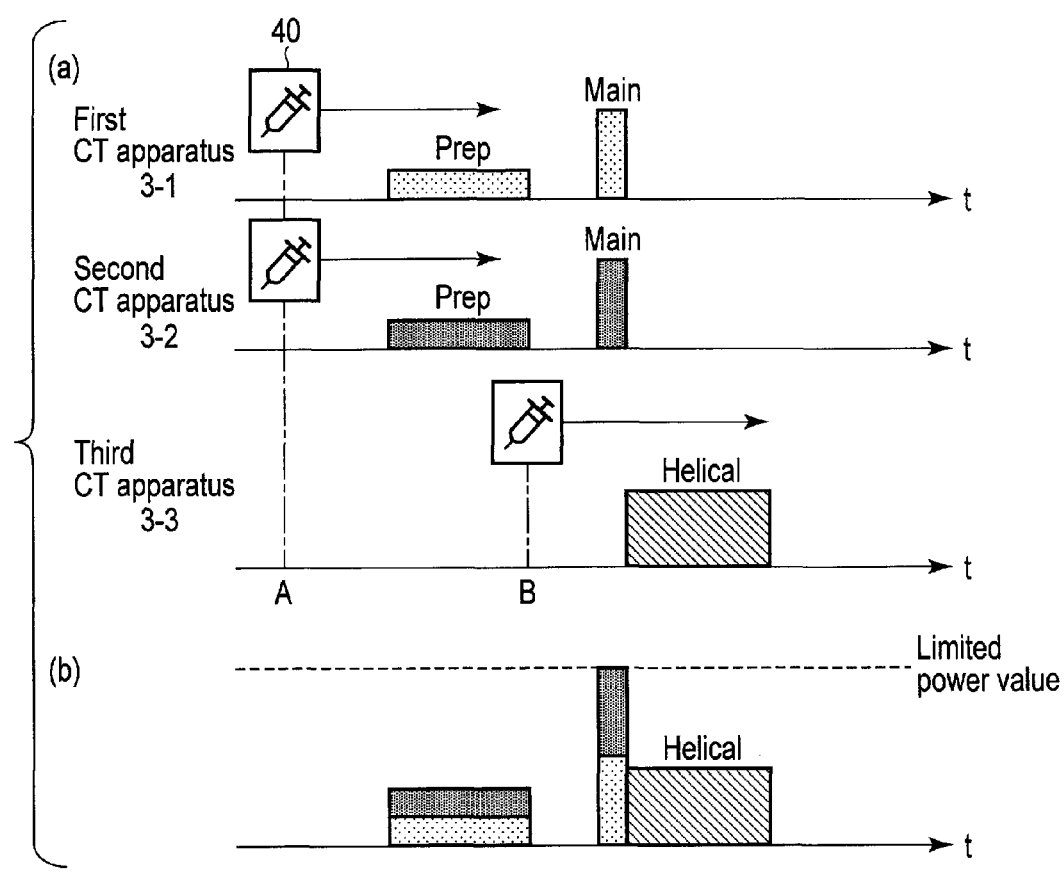
FIG. 5 shows an example of the timing of using an injector connected to an X-ray CT apparatus which is used to inject a contrast medium in this embodiment.

A medical apparatus comprises an apparatus main body configured to execute imaging or treatment of an object in accordance with an imaging plan or a treatment plan, an electric power calculation unit configured to calculate an electric power required for the imaging or the treatment based on the imaging plan or the treatment plan, a reception unit configured to receive power information from a plurality of other medical apparatuses, a total electric power calculation unit configured to calculate a total electric power from the calculated electric power and the received electric power, a comparing unit configured to compare the calculated total electric power with a threshold, and a display unit configured to display a comparison result obtained by the comparing unit.

A medical system according to an embodiment will be described with reference to FIG. 1. The medical system includes a server apparatus 7, a plurality of medical apparatuses 2 to 6, each of which executes imaging or treatment of an object in accordance with an imaging plan or a treatment plan, and an electric communication line 1 such as a hospital LAN which connects the server apparatus 7 to the medical apparatuses 2 to 6 wiredly or wirelessly. The medical apparatuses 2 to 6 include, for example, an X-ray diagnostic apparatus, X-ray CT apparatus, magnetic resonance diagnostic apparatus, radiotherapy apparatus, and X-ray cardiovascular imaging apparatus. A central hospital and the like are often equipped with a plurality of X-ray diagnostic apparatuses and a plurality of X-ray CT apparatuses.

An X-ray diagnostic apparatus 2, an X-ray CT apparatus 3, a magnetic resonance diagnostic apparatus 4, and a radiotherapy apparatus 5 receive power from a power supply system 8. A group of the plurality of medical apparatuses 2 to 5 which receive power supplied from the single power supply system 8 will be referred to as a "group". An X-ray cardiovascular imaging apparatus 6 receives power from another power supply system 9. The operating power upper limits (limited power values) of the power supply systems 8 and 9 are set to the same value or different values. When the total power sum of the power supply system 8 for the X-ray diagnostic apparatus 2, the X-ray CT apparatus 3, the magnetic resonance diagnostic apparatus 4, and the radiotherapy apparatus 5 exceeds the limited power value, the power supply system 8 stops supplying power. The same applies to the power supply system 9.

The server apparatus 7 includes a control unit 71, a communication unit 72, a transmission/reception management unit 74, and a storage unit 75. The transmission/reception management unit 74 manages the transmission/reception of information between the transmission/reception management unit 74 and the medical apparatuses 2 to 6. Typically, the transmission/reception management unit 74 receives power information required for imaging or treatment in accordance with an imaging plan or treatment plan from the medical apparatuses 2 to 6, and transmits, to each of the medical apparatuses 2 to 6, power information associated with remaining ones of the medical apparatuses 2 to 6. The storage unit 75 of the server apparatus 7 stores power information received from the medical apparatuses 2 to 6. Note that power information scheduled in the self apparatus 2 among the medical apparatuses 2 to 5 installed in the same power supply system 8 will be referred to as "second power information" hereinafter, and power information scheduled in, for example, another apparatus 3 among the medical apparatuses 2 to 5 will be referred to as "first power information" hereinafter.

FIG. 2 shows the arrangement of the X-ray CT apparatus 3 in FIG. 1. The X-ray CT apparatus 3 includes a gantry 11 as an apparatus main body which acquires data from an object. The gantry 11 includes a rotating ring 12 which is rotatably supported. An X-ray tube 13 and an X-ray detector 14 are mounted on the rotating ring 12. The X-ray detector 14 faces the X-ray tube 13 through the rotation center axis of the rotating ring 12. The rotating ring 12 has an opening portion in its center. An object P placed on a top 15 of a bed is inserted into the opening portion.

The X-rays emitted from the X-ray tube 13 are transmitted through the object P and detected by the X-ray detector 14 upon being attenuated. The detected X-rays are converted into an electrical signal. A data acquisition unit 16 amplifies the signal and converts it into digital data. This data is sent as projection data to a preprocessing unit 21 via a data transmission unit 17. The preprocessing unit 21 performs processing such as correction of signal intensity and correction of signal loss. An image reconstruction unit 22 reconstructs tomographic image data from preprocessed projection data. The generated tomographic image is displayed on a display 25.

The thermal electrons emitted from the cathode (filament) of the X-ray tube 13 are accelerated and focused by the potential difference between the cathode and the anode and collide with the anode (target), thereby generating X-rays. The potential difference between the cathode and the anode will be referred to as a tube voltage, and thermal electron beam from the cathode will be referred to as a tube current. The X-ray conversion efficiency is very low, and 99% or more of input energy (tube voltage×tube current) is converted into heat. For this reason, the X-ray tube 13 is heated to a very high temperature during operation, and it is necessary to cool the tube with a fan or heat exchanger. This makes it necessary for the X-ray CT apparatus 3 to use a large amount of power for data acquisition, especially for X-ray emission. Likewise, the X-ray diagnostic apparatus 2 and the radiotherapy apparatus 5 require a large amount of power. The magnetic resonance imaging apparatus 4 requires a large amount of power especially for high magnetic field generation and coil cooling.

A scan plan setting support unit 27 tentatively makes a scan plan (imaging plan) in accordance with the imaging purpose, imaging region, and the like designated by a doctor. Finally, the doctor confirms the tentative imaging plan without any change or upon modifying it as needed. Note that an imaging plan before confirmation is called a draft imaging plan, and a confirmed imaging plan is simply called an imaging plan. A power calculation unit 29 calculates a scheduled electric power at each given time during an imaging period in a draft imaging plan based on tube currents, tube voltages, and X-ray duration times of the draft imaging plan. Typically, the power calculation unit 29 calculates a scheduled electric power in minutes.

An intra-group apparatus power information requesting unit 28 requests the server apparatus 7 to provide power information (first power information) concerning other medical apparatuses 2, 4, and 5 in a group associated with the same time during an imaging period in a draft imaging plan via a communication unit 23 before the confirmation of an imaging plan. The communication unit 23 receives the power information (first power information) concerning the other medical apparatuses 2, 4, and 5 from the server apparatus 7 in response to the request. A storage unit 26 mainly stores reconstructed image information and also stores the first power information received from the other medical apparatuses 2, 4, and 5 via the server apparatus 7. Note that the power indicated by the first power information of the other medical apparatuses 2, 4, and 5 are generally confirmed.

A total power sum calculation unit 30 calculates a total power sum in the power supply system 8 at each given time during an imaging period in a draft imaging plan from the received first power information concerning the other medical apparatuses 2, 4, and 5 and the scheduled electric power (second power information) calculated by the power calculation unit 29 of the self apparatus 3 at the stage of making an imaging plan. An upper threshold comparing unit 31 compares the calculated total power sum with the upper limit electric power (limited power value) defined for the power supply system 8. If the total power sum exceeds the limited power value, the upper threshold comparing unit 31 inhibits the scan plan setting support unit 27 from confirming the imaging plan. If total power sum is equal to or less than the limited power value, the upper threshold comparing unit 31 permits the scan plan setting support unit 27 to confirm the imaging plan.

When the upper threshold comparing unit 31 inhibits the confirmation of the imaging plan, the scan plan setting support unit 27 generates a revision of the imaging plan. For example, the scan plan setting support unit 27 prolongs the imaging time width by shifting the X-ray generation time or decreasing the X-ray intensity. This revision will be described in detail below.

A control unit 24 controls the operation of the gantry 11 to perform a prep scan or main scan in accordance with the confirmed imaging plan. In this case, a prep scan is a scan performed with a low dose to measure a CT value in an ROI (Region Of Interest) set in an arbitrary place. The control unit 24 determines a blood flow speed based on the image obtained by this prep scan. The control unit 24 also decides the wait time from the end of the prep scan to the start of a main scan based on the determined blood flow speed.

That is, the control unit 24 measures the timing at which the contrast medium administered in the object P flows into a slice of interest and shifts to a main scan when the CT value exceeds a threshold. The control unit 24 then outputs a guidance concerning the main scan in synchronism with the start timing of the main scan which is determined by the above wait time. In addition, the control unit 24 decides the moving velocity of the top 15 in a direction along the rotation axis in the main scan based on the determined blood flow speed. In contrast, a main scan is a scan to acquire CT values required to reconstruct a tomographic image of the contrast-enhanced object P. In this case, the top 15 needs to move at the time of a helical scan as well as when being inserted into the gantry 11.

FIG. 3 shows the power information of a draft imaging plan in the X-ray CT apparatus 3 in chronological order. For the sake of descriptive convenience, the following description will be made on a case in which three X-ray CT apparatuses 3-1, 3-2, and 3-3 are connected to the same power supply system 8. Assume that the apparatus 3-3 is the self apparatus at the stage of making an imaging plan.

When, for example, performing contrast medium examination, the apparatus generally performs a preliminary scan (also called a prep scan) before a main scan to perform timing control on the main scan. The apparatus performs a prep scan to check how a contrast medium flows in an object. "Prep" and "Main" in FIG. 3 respectively represent a prep scan and a main scan. A prep scan can fulfill its role with a minimum dose, and hence is smaller in dose than a main scan. For this reason, the power to be applied to the X-ray tube 13 can be smaller than that for a main scan. This makes it possible to use the apparatus with low power, as shown in FIG. 3.

Although an injector for injecting a contrast medium into the object P is also connected to the other X-ray CT apparatuses 3-1 and 3-2, a description concerning the injector will be omitted. Control on the injection of a contrast medium by the injector will be described later with reference to FIG. 5.

In FIG. 3, (a) is a schematic view of the information of power scheduled to be used by the first to third CT apparatuses 3-1, 3-2, and 3-3. In this case, as indicated by (b) in FIG. 3, the power used by only the CT apparatuses 3-1 and 3-2 will reach the limited power value.

In the description of this embodiment, when the operator uses a given apparatus, the power information of the other apparatuses 3-1 and 3-2 scheduled to be used, which is stored in the server apparatus 7, will be called first power information, and power information of the apparatus which the operator intends to use will be called second power information. In this case, information concerning the operating power of the first and second CT apparatuses 3-1 and 3-2 is the first power information, and information concerning the operating power of the third CT apparatus 3-3 is the second power information. Note that when, for example, the operator uses the fourth CT apparatus (not shown), the second power information becomes the first power information when it is stored in the server apparatus 7, and information concerning the operating power of the fourth CT apparatus which is to be notified to the server apparatus 7 is called the second power information.

When the operator simultaneously uses the first and second CT apparatuses 3-1 and 3-2, the sum of operating power values of the first and second CT apparatuses 3-1 and 3-2 reaches the limited power value at the time of a main scan, as indicated by (b) in FIG. 3. If the operator uses the third CT apparatus 3-3 at the timing indicated by (b) in FIG. 3, the sum of operating power values exceeds the limited power value. For this reason, the timing of using the third CT apparatus 3-3 is automatically shifted in accordance with the first power information from the server apparatus 7 so as not to exceed the limited power value. Therefore, upon determining the use schedule of each apparatus, the operator performs operation to notify the server apparatus 7 of the information of the use schedule of each apparatus in advance. The operator performs this operation by operating an information input means (not shown) or the like. Based on this information, the communication unit 23 notifies the server apparatus 7 of the corresponding information.

When the operator uses the third CT apparatus 3-3, the communication unit 23 communicates with the server apparatus 7 to acquire the first power information of the other apparatuses (the first and second CT apparatuses 3-1 and 3-2 in this case) in the power supply system 8. When the first power information is almost the limited power value as indicated by (b) in FIG. 3, the timing of using the third CT apparatus 3-3 is shifted instead of allowing to use the third CT apparatus 3-3 at the initially scheduled timing. At this time, the communication unit 23 of the third CT apparatus 3-3 notifies the server apparatus 7 of the information of the use timing.

FIG. 4 is a schematic view showing the first power information notified to the server apparatus 7 based on the assumption of variations in the time at which prep scans and main scans are performed by the first and second CT apparatuses 3-1 and 3-2. As described above, a prep scan is a scan method of monitoring a contrast enhancement effect after the injection of a contrast medium, and hence the imaging time (the power using time) differs depending on the arrival timing of the contrast medium.

It is therefore conceivable to use power information with margins in the end timings of scans like patterns A to D depending on the object P or the state of the object P. Referring to FIG. 4, a difference A–B in arrival timing between a timing A in which the arrival timing of a contrast medium is the earliest and a pattern D in which the arrival timing of the contrast medium is the latest is considered as the width of variations. In this case, in order to prevent the limited power value from being exceeded in any case, it is preferable to set the width of variations so as to cover any operating power within the range of the worst pattern of the patterns A to D as shown in FIG. 4. The communication unit 23 notifies the server apparatus 7 of the first power information. Note that the width of variations in arrival timing may be set to a preset value or may be set based on past measurement results.

For the sake of simplicity, FIGS. 3, 5, 6, 8, and 9 show any information in consideration of the above worst pattern. It is, however, preferable to notify the server apparatus 7 of the first power information in consideration of the worst pattern when using apparatuses accompanying prep scans.

FIG. 5 is a schematic view showing the first power information in the first and second CT apparatuses 3-1 and 3-2 in chronological order. An injector as a peripheral device is connected to each X-ray CT apparatus 3. The following will exemplify a case in which an injector 40 for injecting a contrast medium is used as a peripheral device.

When using the third CT apparatus 3-3, it is necessary to inject a contrast medium before performing a scan. The doctor may manually inject a contrast medium at the start timing or it is possible to automatically inject the contrast medium at the timing (A) upon preparing for injection in advance. In addition, since it is necessary to perform scans at predetermined intervals after the injection of the contrast medium, it is not preferable to perform scans at larger intervals in accordance with the state of power after the injection of the contrast medium or perform a scan immediately after the injection of the contrast medium.

In this embodiment, therefore, the third CT apparatus 3-3 also controls the injection timing of a contrast medium by the injector 40 connected to the third CT apparatus 3-3 based on the first power information of the first and second CT apparatuses 3-1 and 3-2. More specifically, the timing of a helical scan is determined so as not to exceed the limited power. Based on this timing, the timing (B) of the injection of a contrast medium is determined.

In addition, as shown in FIG. 5, likewise when executing a helical scan after the injection of an contrast medium without performing a prep scan, the apparatus executes a helical scan at a predetermined timing after the injection of the contrast medium without shifting the timing of a helical scan.

As described above, the first power information of the first and second CT apparatuses 3-1 and 3-2 which perform prep scans is information with the consideration of variations in the time required for each prep scan. Therefore, it is highly possible that the use of the first or second CT apparatus 3-1 or 3-2 comes to an end before the timing indicated by the first power information acquired from the server before the timing (B) of the third CT apparatus 3-3. In consideration of this, when using the third CT apparatus 3-3 at an earlier timing, it is preferable to prepare for the use of the apparatus assuming that a contrast medium is injected at an earlier timing than the initially scheduled timing. It is therefore preferable that at the timing of the end of a prep scan, each of the first and second CT apparatuses 3-1 and 3-2 simultaneously notifies the server apparatus 7 of the corresponding information, and the server apparatus 7 notifies the third CT apparatus 3-3 of the data obtained by updating the information. The operator may start using the third CT apparatus 3-3 at an earlier timing than the initially scheduled timing or at the initially scheduled timing based on the data notified from the server. When starting using the apparatus at an earlier timing, since the timing differs from that indicated by the second power information previously notified to the server apparatus 7, it is necessary to newly notify the server apparatus 7 of the updated information.

Alternatively, it is possible to execute a scan with low power so as not to exceed the limited power value instead of shifting the timings of the injection of a contrast medium and each scan by the third CT apparatus 3-3.

FIG. 6 is a schematic view showing a case in which apparatuses are used with low power (low dose) in this embodiment. In FIG. 6, (a) is a schematic view of the information of power scheduled to be used by the first to third CT apparatuses 3-1, 3-2, and 3-3 as in the case indicated by (a) in FIG. 3. As indicated by (b) in FIG. 6, the sum of the power values exceeds the limited power value.

It is therefore preferable to shift the start timings of scans. In some cases, however, the operation may be changed to low-power operation as indicted by (c) in FIG. 6. As in the case shown in FIG. 3, based on the first power information notified from the server apparatus 7, the third CT apparatus 3-3 performs a scan with power enough not to exceed the power limit value.

The use of the X-ray CT apparatus 3 with low power will be described in detail below.

The use of the apparatus with low power indicates the use of the apparatus while reducing power to be applied to the X-ray tube 13. This leads to imaging with a low dose. In order to obtain an image with the same image quality as that initially planned, the emission time (scan time width) may be increased as indicated by (c) in FIG. 6. In addition, with a reduction in dose, the rotational velocity of the rotating ring 12 and the moving velocity of the top 15 in the gantry 11 are decreased. This makes it possible to use the third CT apparatus 3-3 without exceeding the limited power value as indicated by (d) in FIG. 6.

As in the case described with reference to FIG. 4, the timing of using the third CT apparatus 3-3 is determined based on the first power information. In this case, however, the operating power of the third CT apparatus 3-3 is reduced so as not to exceed the power limit value. At this time, the third CT apparatus 3-3 acquires in advance the first power information from the server apparatus 7 before the injection of a contrast medium which is associated with the use of the self apparatus, and checks how much margin of power is available between the limited power value and the power scheduled to be used by the first and second CT apparatuses 3-1 and 3-2. In this case, upon determining that the apparatus allows use with low power without shifting any timing, the apparatus notifies the server apparatus 7 of the use with low power. Using the apparatus with low power makes it necessary to prolong the emission time. This makes it necessary to give more consideration to the problem of breath holding and body movement of an object. The operator may perform this determination based on experience on the spot or may let the apparatus automatically determine from the value of the difference between the limited power value and the sum of power used by the first and second CT apparatuses 3-1 and 3-2 upon setting, on the apparatus side, the information "a power value allowing the use of the apparatus with low power without posing any problem".

If the limited power value is exceeded even with the use of the apparatus with a power value allowing the use of the apparatus with low power without posing any problem due to the above problem of breath holding or body movement, the timing of using may be changed in the above manner.

The operation of an X-ray CT apparatus according to this embodiment will be described next.

FIG. 7 is a flowchart according to this embodiment. Note that the "initial timing" is the timing at which the operator has shown his/her intention to use the third CT apparatus 3-3 by, for example, operating the information input means for inputting information like the information of the apparatus indicated by (a) in FIG. 3.

In step S1, the control unit 24 of the X-ray CT apparatus 3 connected to the server apparatus 7 makes an inquiry to the server apparatus 7 to acquire the first power information of other apparatuses in the power supply system 8 by using the communication unit 23. In this case, for example, the operator may check the operating power information of the other apparatuses displayed on the display 25 and input information indicating the use of the self apparatus by using an information input means provided in the console. In the case of using the first to third CT apparatuses 3-1 to 3-3 described above, the operator considers using the third CT apparatus 3-3.

In the case of using the first to third CT apparatuses 3-1 to 3-3 described above, the third CT apparatus 3-3 acquires the first power information of the first and second CT apparatuses 3-1 and 3-2 from the server apparatus 7. At this time, as shown in FIG. 2, if it is necessary to perform a prep scan (an examination using a contrast medium), the end timing of the prep scan differs (that is, the start timing of a main scan also differs) depending on the object P or the state of the object P, as described above. For this reason, the server apparatus 7 stores the first power information with the consideration of variations in the end timings of prep scans like that shown in FIG. 4.

The server apparatus 7 stores the first power information transmitted from the first and second CT apparatuses 3-1 and 3-2, and notifies the third CT apparatus 3-3 of the stored first power information in response to a request from the third CT apparatus 3-3.

In this case, when the first and second CT apparatuses 3-1 and 3-2 complete prep scans at earlier timings than those set in consideration of variations, they inform the server apparatus 7 of the corresponding information. At this time, the server apparatus 7 stores the updated information and notifies the third CT apparatus 3-3 of the corresponding information.

Note that it is preferable to perform a prep scan and a main scan at a constant interval. For this reason, the control unit 24 performs control to change the timing of a main scan with a change in the end timing of a prep scan so as to keep the interval between the prep scan and the main scan constant.

In step S2, the upper threshold comparing unit 31 determines, based on the first power information acquired in step S1, whether the total power sum exceeds the limited power at the timing of scheduled use. When using an apparatus requiring a prep scan, the upper threshold comparing unit 31 performs determination based on power information with the consideration of a worst pattern. If the total power sum does not exceed the limited power, the process advances to step S4A. If the total power sum exceeds the limited power, the process advances to step S3.

In the case of using the first to third CT apparatuses 3-1 to 3-3 described above, since the total power sum exceeds the limited power when using the third CT apparatus 3-3 at the initial timing, the process advances to step S3.

In step S3, the control unit 24 determines whether it is possible to use the apparatus with low power that does not cause an excess of the limited power. If it is possible to use the apparatus with low power, the process advances to step S4B. If it is not possible to use the apparatus with low power, the process advances to step S4C.

In the case shown in FIG. 6, the process advances to step S4B. In the case shown in FIG. 3, the process advances to step S4C.

In step S4A, the control unit 24 decides the use of the apparatus with normal power at the initial timing.

In step S4B, the control unit 24 decides the use of the apparatus with low power that does not cause an excess of the limited power value at the initial timing.

In step S4C, the control unit 24 decides the use of the apparatus with normal power at another timing.

Although the control unit 24 automatically decides the timing of use in steps S4A to S4C in this case, the operator may make a final decision.

In step S5, the control unit 24 notifies the server apparatus 7 of power information corresponding to the scheduled use of the X-ray CT apparatus 3-3. In the case of using the first to third CT apparatuses 3-1, 3-2, and 3-3, the third CT apparatus 3-3 notifies the server apparatus 7 of the second power information. The server apparatus 7 updates the first power information stored in advance in consideration of the second power information.

In step S6, the control unit 24 controls the operation of the X-ray CT apparatus 3, e.g., X-ray emission, based on the second power information notified to the server apparatus 7 in step S5.

In this case, as described above, the first and second CT apparatuses 3-1 and 3-2 for diagnosis using a contrast medium complete prep scans at irregular timings. For this reason, the control unit 24 notifies the server apparatus 7 of power information based on the assumption of the variations. However, since the information is set based on the assumption of a worst case in which a prep scan is prolonged, the use of the first or second CT apparatus 3-1 or 3-2 may come to an end at an earlier timing than that indicated by information notified in advance. In this case, if there is no need to inject a contrast medium when using the third CT apparatus 3-3, the operator may start using the third CT apparatus 3-3 at an earlier timing than the use start timing notified in step S3.

This does not apply to a case in which the operator uses the third CT apparatus 3-3 for diagnosis using a contrast medium, and the apparatus performs a main scan after the start of a prep scan. This is because the apparatus performs a main scan a predetermined interval, e.g., 90 sec, after a prep scan. Even if it is possible, in terms of power, to use the apparatus, it is not preferable to perform a main scan at a shortened interval. If the injection of a contrast medium is scheduled for the third CT apparatus 3-3 after the use of the first and second CT apparatuses 3-1 and 3-2, the operator may start injecting a contrast medium for the third CT apparatus 3-3 at an earlier timing after the initial timing after the first or second CT apparatus 3-1 or 3-2 completes a prep scan and the server apparatus 7 notifies the third CT apparatus 3-3 of the corresponding information.

In this case, it is possible, in terms of power, to use the apparatus with lower operating power than the initially scheduled power notified to the server apparatus 7. When using the apparatus with lower power than scheduled power, therefore, the operator may use the apparatus with reduced power according to the initial schedule without notifying the server apparatus 7 of the corresponding information, although the operator may notify the server apparatus 7 of such a change every time it occurs. In contrast, it is not preferable to change the timing of using without notification.

Figure 8:
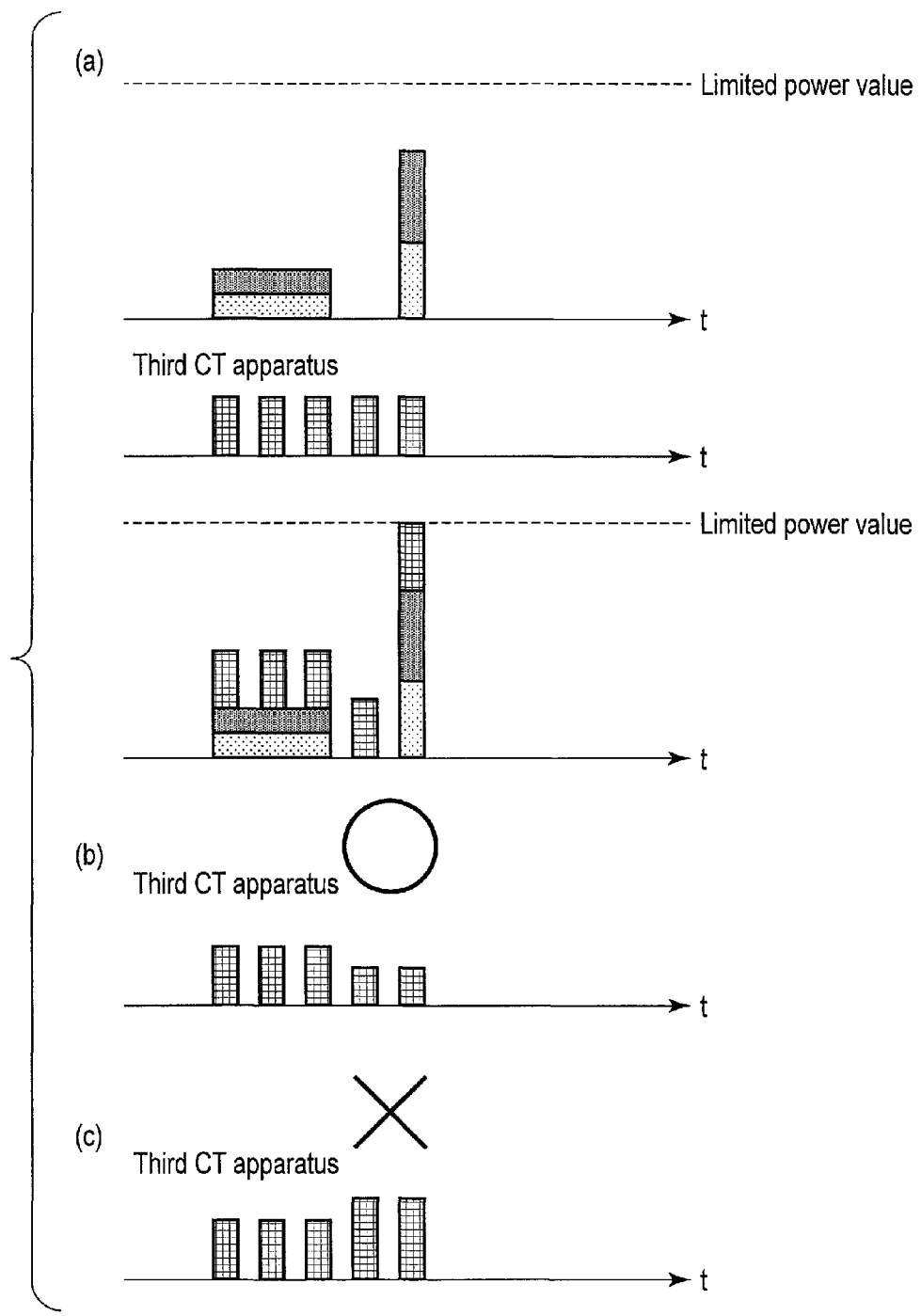
FIG. 8 shows an example of operating power control in this embodiment.

In FIG. 8, (a) is a schematic view showing the power information of a use schedule for the CT apparatus 3-3 of the first to third CT apparatuses. In this case, the third CT apparatus 3-3 performs a main scan in five steps without performing any prep scan. This indicates a case of an ECG scan, respiration gated scan, or the like. As described above, this embodiment can be applied to various types of scan sequences using the X-ray CT apparatuses 3 as well as scan sequences requiring prep scans.

In the case shown in FIG. 8, the total power consumption almost falls within the power limit value, it is possible to use the third CT apparatus 3-3 according to the plan. In this case, as indicated by (b) in FIG. 8, it is possible to reduce the operating power without updating the information notified to the server apparatus 7 after the start of operation of the apparatus. On the other hand, increasing the operating power without updating the information will cause an excess of the power limit value, and hence it is not possible to increase the operating power without updating the information ((c) in FIG. 8).

Although this embodiment has exemplified the case of using the X-ray CT apparatuses 3, this embodiment is not limited to this. It is possible to use modalities different from X-ray CT apparatuses and manage power information of the other modalities by using the server.

Consider, for example, a case in which an MRI (Magnetic Resonance Imaging) apparatus is connected to a network. In this case, since the MRI apparatus requires a longer imaging time than an X-ray CT apparatus, the operating power of the MRI apparatus greatly influences the use of other apparatuses.

Figure 9:
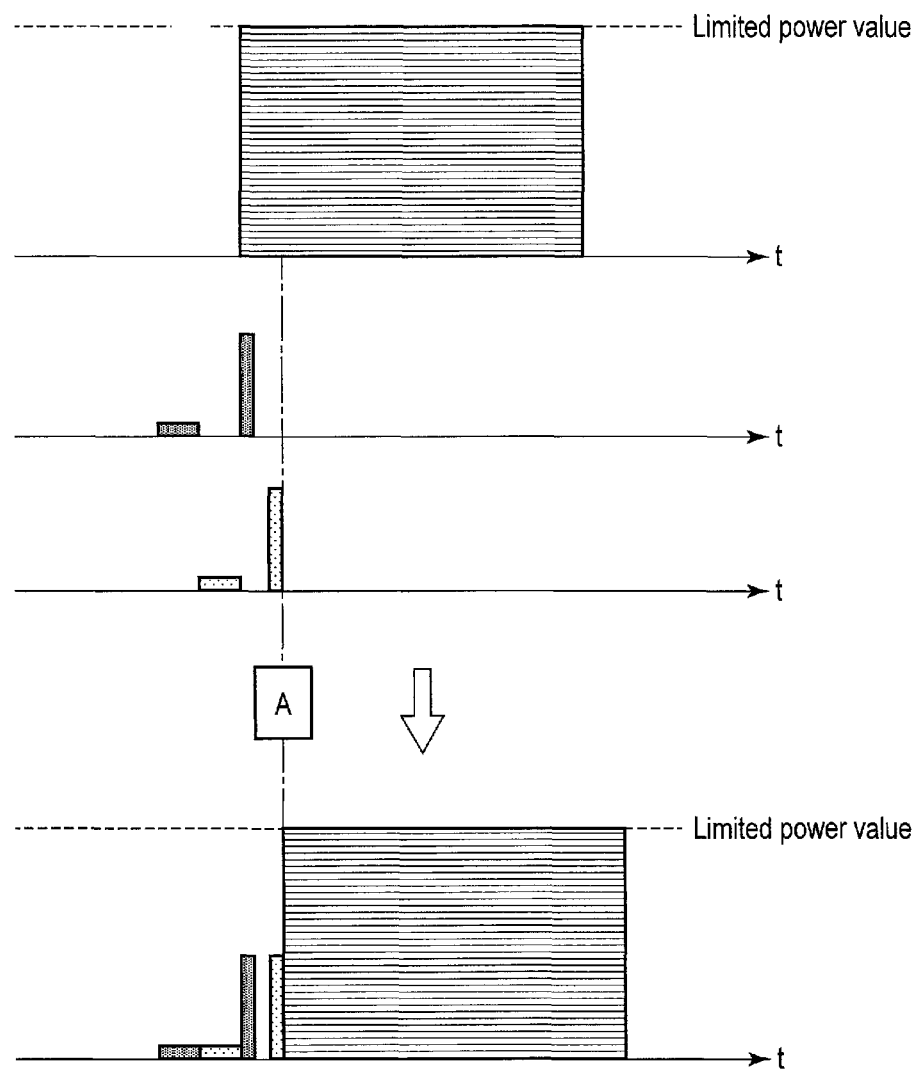
FIG. 9 is a schematic view showing an example of postponing the use of the X-ray CT apparatus scheduled to be used in this embodiment.

If, therefore, it is obvious from the use schedule of the MRI apparatus that the operating power is almost the limited power, the initially scheduled timing of using the MRI apparatus may be shifted to a timing A as indicated by (b) in FIG. 9 while giving priority of use of power to a CT apparatus and other apparatuses with short imaging times. More specifically, if the second or third CT apparatus 3-2 or 3-3 is scheduled to be used at the timing indicated by (a) in FIG. 9, a request is made to postpone the use of the MRI apparatus. It is possible to make this request via the server or directly between the apparatuses. Upon receiving the request, the MRI apparatus returns, if it is possible to postpone, corresponding information to the server or the apparatus which has made the request.

This embodiment has exemplified the case in which the server apparatus 7 is provided outside the X-ray CT apparatus 3. However, the embodiment is not limited to this. The X-ray CT apparatus 3 or the like may incorporate a server.

Note that there are apparatuses, other than the first to third CT apparatuses 3-1, 3-2, and 3-3, which use power, and hence power information can be more complicated. Although this embodiment has exemplified only the three apparatuses, the embodiment can be applied to a larger number of apparatuses to be used.

The effects of X-ray CT apparatuses according to this embodiment will be described next.

According to this embodiment, the server apparatus 7 manages power information of each of the plurality of X-ray CT apparatuses 3 connected to the server apparatus 7 to allow the use of medical apparatuses such as the X-ray CT apparatuses 3 without exceeding the power limit value. Since it is possible to use each apparatus without exceeding the power limit value, it is possible to obtain a diagnostic image with desired image quality.

In addition, this embodiment automatically control the timing of a scan period, and hence implements efficient use of apparatuses as well as avoiding an excess of the power limit value. Since it is inadequate from a diagnostic point of view to stop using a medical apparatus during diagnosis, the embodiment which can automatically control the timing of using is very effective and can be applied to any types of hospitals and health clinics.

In addition, as described above, since the end timing of a prep scan accompanying the injection of contrast medium is indefinite, the end timing of a prep scan is initially set within a certain range. Updating the information simultaneously with the end of the prep scan afterward can implement more efficient use of each apparatus without any unnecessary delays.

In addition, this embodiment controls the timing of using a peripheral device connected to the X-ray CT apparatus 3 to implement more preferable diagnosis for the operator and the patient. More specifically, since the timing of injecting a contrast medium by using an injector can be automatically derived from the timing of a scan, the operator can safely inject the contrast medium without worrying about power shortage, and can perform a scan at a more suitable timing.

Assume that when performing a scan at a suitable timing after the injection of a contrast medium, the limited power is exceeded. In this case, the operator needs to forcibly use the apparatus with low power or wait until the power becomes sufficient. This raises the problems that it is impossible to obtain desired image quality with the use of low power and missing the optimal scan timing after the injection of the contrast medium leads to an inadequate image. This embodiment can solve the above problems.

In addition, as described with reference to FIG. 6, using a given apparatus with low power according to the situation allows the use of the apparatus without shifting a desired timing. Referring to FIG. 6, it is possible to use the third CT apparatus 3-3 after the end of the use of the first and second CT apparatuses 3-1 and 3-2. In some cases, however, the operator may need to wait for several ten min because of the use of power by other apparatuses. In such a case, if it is necessary to urgently use the third CT apparatus 3-3 for an emergency patient or the like, the operator must use the apparatus with low power as soon as possible. For such cases, this embodiment is very useful because it can manage the use of power by a plurality of apparatuses in the power supply system 8 and adjust the timing at which each apparatus can be used with low power based on the management.

When using other modalities such as MRI apparatuses, it is possible to efficiently use each apparatus by letting the server apparatus 7 manage power information. Providing priority levels in advance allows the efficient use of each apparatus by letting the operator use a CT apparatus or the like with a high priority level during a period in which, for example, an MRI apparatus is scheduled to be used. When combining an MRI image with a CT image in visualization of data after imaging operation, it is possible to adjust the timing of combining processing.

Figure 10:
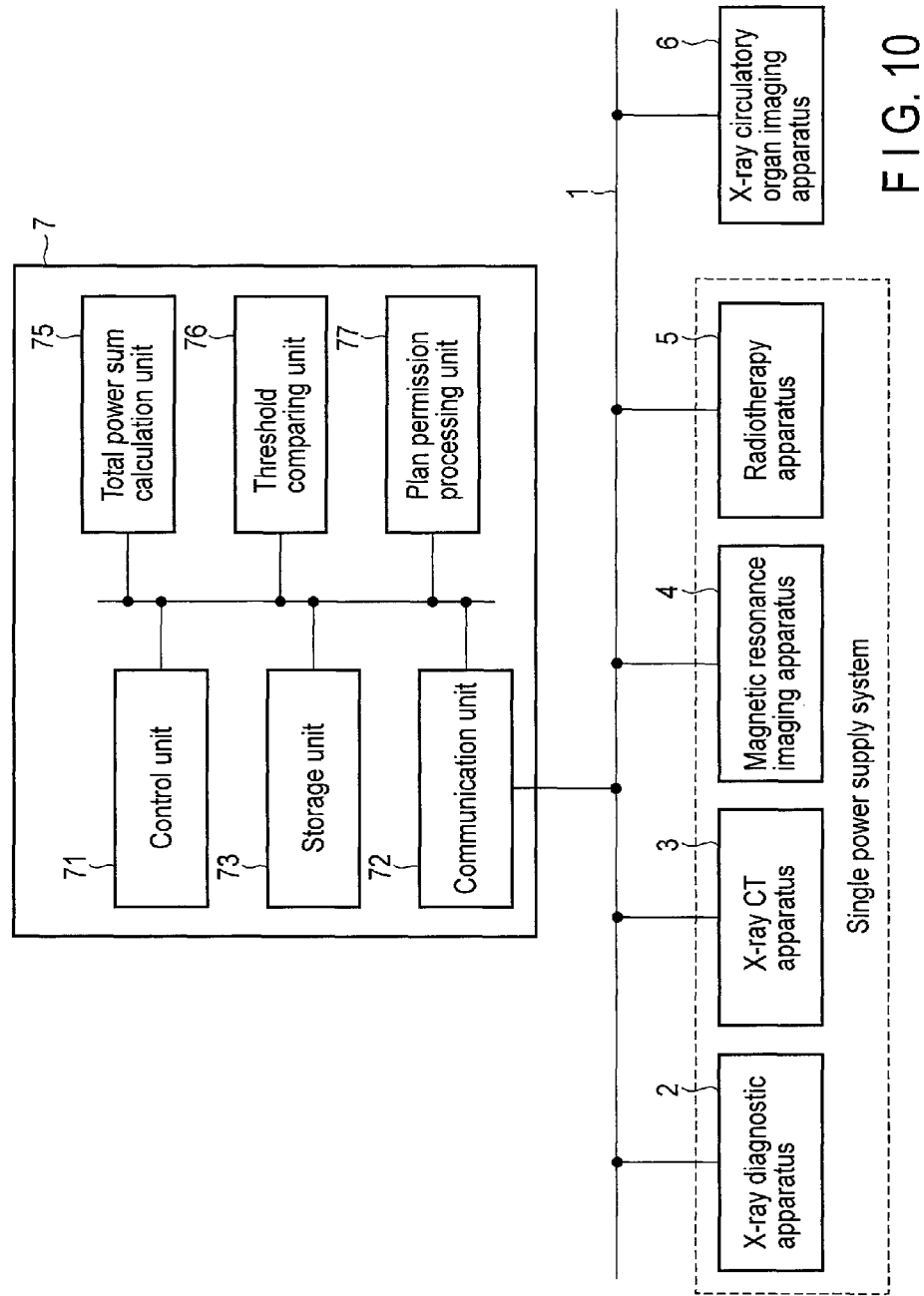
FIG. 10 is a block diagram showing another overall arrangement of the medical system according to this embodiment.

The above description has exemplified the case in which each medical apparatus executes total power sum calculation processing, threshold comparison processing, and inhibition/permission of confirmation of an imaging plan. As shown in FIG. 10, however, the server apparatus 7 may execute them. A control unit 71 of the server apparatus 7 requests, via a communication unit 72, all the medical apparatuses 2 to 6 connected to each other via a LAN 1 to transmit power information. A storage unit 73 stores the power information transmitted from medical apparatuses 2 to 6.

Assume that the medical apparatus 3 at the stage of making an imaging plan requests the server apparatus 7 to permit confirmation of the plan, a total power sum calculation unit 75 of the server apparatus 7 calculates a total power sum in the power supply system 8 for each given time during an imaging period in a draft imaging plan for the medical apparatus 3 from power information from the other medical apparatuses 2, 4, and 5 in the same power supply system 8 as that to which the medical apparatus belongs and power information from the medical apparatus X-ray CT apparatus 3. A threshold comparing unit 76 compares the calculated total power sum with the upper electric power (limited power value) specified for the power supply system 8. If the total power sum exceeds the limited power value, a plan permission processing unit 77 transmits a control signal to the X-ray CT apparatus 3 via the communication unit 72 to inhibit the confirmation of the imaging plan. Upon receiving a control signal for permitting the confirmation of the imaging plan, the scan plan setting support unit 27 of the medical apparatus 3 activates the confirmation button on the imaging plan window displayed on the display 25. Upon receiving the control signal for inhibiting the confirmation of the imaging plan, the scan plan setting support unit 27 of the X-ray CT apparatus 3 keeps the confirmation button inactive on the imaging plan window displayed on the display 25. Every time revising the imaging plan for the medical apparatus 3, the operator requests the server apparatus 7 to permit the confirmation of the plan. The operator repeatedly revises an imaging plan and issues a request to permit confirmation until the apparatus receives a control signal for permitting the confirmation of the imaging plan from the server apparatus 7.

According to the above description, the medical apparatus side generates a revision of an imaging plan. However, the server apparatus 7 may generate a revision of an imaging plan. In this case, the server apparatus 7 transmits the revision of the imaging plan to the medical apparatus, together with a control signal to inhibit the confirmation of the imaging plan.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical system comprising a server apparatus, a plurality of medical apparatuses configured to execute imaging or treatment of an object in accordance with an imaging plan or a treatment plan, and an electric communication line configured to connect the server apparatus to the medical apparatuses, each of the medical apparatuses comprising an electric power calculation unit configured to calculate an electric power required for the imaging or the treatment based on the imaging plan or the treatment plan, a reception unit configured to receive amount of power from a plurality of other medical apparatuses via the server apparatus, a total electric power calculation unit configured to calculate a total electric power from the calculated electric power and the received electric power, a comparing unit configured to compare the calculated total electric power with a threshold, and a display configured to display a comparison result obtained by the comparing unit.

2. The medical system of claim 1, wherein the display displays a message for prompting to revise the imaging plan or the treatment plan when the total electric power exceeds the threshold.

3. The medical system of claim 1, wherein each of the medical apparatuses comprises an imaging plan revision support unit configured to change a timing of the imaging or the treatment or reduce the electric power so as to generate a revision plan of the imaging plan or the treatment plan, when the total electric power exceeds the threshold.

4. A medical system comprising a server apparatus, a plurality of medical apparatuses configured to execute imaging or treatment of an object in accordance with an imaging plan or a treatment plan, and an electric communication line configured to connect the server apparatus to the medical apparatuses, the server apparatus comprising a reception unit configured to receive amount of power required for the imaging or the treatment in accordance with the imaging plan or the treatment plan from the plurality of medical apparatuses;

a total electric power calculation unit configured to calculate a total electric power from the received electric power;

a comparing unit configured to compare the calculated total electric power with a threshold; and a transmission unit configured to transmit a comparison result obtained by the comparing unit to the plurality of medical apparatuses.

5. The medical system of claim 4, wherein the transmission unit transmits a signal for permitting the imaging plan or the treatment plan to one of the medical apparatuses when the total electric power does not exceed the threshold, and transmits a command for prompting to transmit a signal for prompting to revise the imaging plan or the treatment plan to one of the medical apparatuses when the total electric power exceeds the threshold.

6. The medical system of claim 4, wherein each of the medical apparatuses further comprises an imaging plan revision support unit configured to change a timing of the imaging or the treatment or reduce the electric power so as to generate a revision plan of the imaging plan or the treatment plan, upon reception of a signal for prompting to revise the imaging plan or the treatment plan from the server apparatus.

7. A server apparatus connected, via an electric communication line, to a plurality of medical apparatuses configured to execute imaging or treatment of an object in accordance with an imaging plan or a treatment plan, comprising:

a reception unit configured to receive amount of power required for the imaging or the treatment in accordance with the imaging plan or the treatment plan from the plurality of medical apparatuses;

a total electric power calculation unit configured to calculate a total electric power from the received electric power;

a comparing unit configured to compare the calculated total electric power with a threshold; and a transmission unit configured to transmit a comparison result obtained by the comparing unit to the plurality of medical apparatuses.

8. A power management method for a medical system comprising a server apparatus, a plurality of medical apparatuses configured to execute imaging or treatment of an object in accordance with an imaging plan or a treatment plan, and an electric communication line configured to connect the server apparatus to the medical apparatuses, comprising, in the server apparatus, receiving amount of power required for the imaging or the treatment in accordance with the imaging plan or the treatment plan from the plurality of medical apparatuses;

calculating a total electric power from the received electric power;

comparing the calculated total electric power with a threshold; and transmitting a comparison result between the calculated total electric power and the threshold to the plurality of medical apparatuses.

9. A power management method for a server apparatus connected, via an electric communication line, to a plurality of medical apparatuses configured to execute imaging or treatment of an object in accordance with an imaging plan or a treatment plan, comprising:

receiving amount of power required for the imaging or the treatment in accordance with the imaging plan or the treatment plan from the plurality of medical apparatuses;

calculating a total electric power from the received electric power;

comparing the calculated total electric power with a threshold; and transmitting a comparison result between the calculated total electric power and the threshold to the plurality of medical apparatuses.

10. An X ray CT apparatus including an X ray tube configured to emit X rays to an object and an X ray detector disposed to face the X ray tube and configured to detect the X rays, comprising:

a communication unit configured to obtain first amount of power as information of power for an apparatus different from the X ray CT apparatus; and a control unit configured to determine second amount of power as information of power for the X ray CT apparatus based on the first amount of power and control a scan timing of performing a scan by emission of X rays from the X ray tube based on the determined second amount of power, wherein the control unit controls the scan timing so as to maintain an interval between a plurality of scans in the X ray CT apparatus.

11. An X ray CT apparatus including an X ray tube configured to emit X rays to an object and an X ray detector disposed to face the X ray tube and configured to detect the X rays, comprising:

a communication unit configured to obtain first amount of power as information of power for an apparatus different from the X ray CT apparatus; and a control unit configured to determine second amount of power as information of power for the X ray CT apparatus based on the first amount of power and control a scan timing of performing a scan by emission of X rays from the X ray tube based on the determined second amount of power, wherein the control unit controls the scan timings of a plurality of scans by comparison with a limited power value in each of the plurality of scans.

12. An X ray CT apparatus including an X ray tube configured to emit X rays to an object and an X ray detector disposed to face the X ray tube and configured to detect the X rays, comprising:
   a communication unit configured to obtain first amount of power as information of power for an apparatus different from the X ray CT apparatus; and
   a control unit configured to determine second amount of power as information of power for the X ray CT apparatus based on the first amount of power and control a scan timing of performing a scan by emission of X rays from the X ray tube based on the determined second amount of power, wherein the control unit controls the scan timings of a prep scan for monitoring arrival of a contrast medium and a main scan started at a predetermined interval after an end of the prep scan.

13. An X-ray CT apparatus including an X-ray tube configured to emit X-rays to an object and an X-ray detector disposed to face the X-ray tube and configured to detect the X-rays, comprising:
   a communication unit configured to obtain first amount of power as information of power for an apparatus different from the X-ray CT apparatus; and
   a control unit configured to determine second amount of power as information of power for the X-ray CT apparatus based on the first amount of power and control a scan timing of performing a scan by emission of X-rays from the X-ray tube based on the determined second amount of power,
   wherein the control unit controls the scan timings based on a width of variations in scan timing of a scan for the object in which a contrast medium has been injected.

14. An X ray CT apparatus including an X ray tube configured to emit X rays to an object and an X ray detector disposed to face the X ray tube and configured to detect the X rays, comprising:
   a communication unit configured to obtain first amount of power as information of power for an apparatus different from the X ray CT apparatus; and
   a control unit configured to determine second amount of power as information of power for the X ray CT apparatus based on the first amount of power and control a scan timing of performing a scan by emission of X rays from the X ray tube based on the determined second power information,
   wherein the communication unit notifies the other apparatuses of the second power information.

15. An X-ray CT apparatus including an X-ray tube configured to emit X-rays to an object and an X-ray detector disposed to face the X-ray tube and configured to detect the X-rays, comprising:
   a communication unit configured to obtain first amount of power as information of power for an apparatus different from the X-ray CT apparatus; and
   a control unit configured to determine second amount of power as information of power for the X-ray CT apparatus based on the first amount of power and control a scan timing of performing a scan by emission of X-rays from the X-ray tube based on the determined second amount of power,
   wherein the control unit also controls an operation timing of a peripheral device connected to the X ray CT apparatus.

16. The X ray CT apparatus of claim 15, wherein the peripheral device comprises an injector configured to inject a contrast medium into an object, and
   the control unit controls the injector based on the scan timing.

17. An X ray CT apparatus including an X ray tube configured to emit X rays to an object and an X ray detector disposed to face the X ray tube and configured to detect the X rays, comprising:
   a communication unit configured to obtain first amount of power as information of power for an apparatus different from the X ray CT apparatus; and
   a control unit configured to determine second amount of power as information of power for the X ray CT apparatus based on the first amount of power and control a scan timing of performing a scan by emission of X rays from the X ray tube based on the determined second amount of power,
   wherein the control unit performs control to prolong a time during which a scan is performed, decrease power to be applied to the X ray tube, and decrease a moving velocity of a top so as not to exceed a limited power value, based on the first power information.

18. A medical system in which a server is connected to a plurality of medical apparatuses via a communication line,
   wherein the plurality of medical apparatuses comprise communication units configured to notify the server of pieces of amount of power of the self medical apparatuses by communicating with the server,
   the server notifies the plurality of medical apparatuses of a sum of the amount of power of the plurality of medical apparatuses, and
   the plurality of medical apparatuses comprise control units configured to control timings of using self medical apparatuses based on a notification from the server.

19. A medical system server which is configured to be connected to a plurality of medical apparatuses via a communication line and comprises a communication unit and a storage unit,
   wherein the communication unit is configured to receive amount of power of the plurality of medical apparatuses from the respective medical apparatuses and transmit, to the plurality of medical apparatuses, data stored by the storage unit upon addition of the power amount of, every time the storage is performed.

* * * * *